United States Patent
Steen et al.

(10) Patent No.: US 7,604,595 B2
(45) Date of Patent: Oct. 20, 2009

(54) METHOD AND SYSTEM FOR PERFORMING REAL TIME NAVIGATION OF ULTRASOUND VOLUMETRIC DATA

(75) Inventors: Erik Normann Steen, Moss (NO); Rune Torkildsen, Foreidgren (NO); Ditlef Martens, Bergen (NO)

(73) Assignee: General Electric Company, Schenectady, NY (US)

( * ) Notice: Subject to any disclaimer, the term of this patent is extended or adjusted under 35 U.S.C. 154(b) by 912 days.

(21) Appl. No.: 10/926,547

(22) Filed: Aug. 26, 2004

(65) Prior Publication Data

US 2005/0283079 A1 Dec. 22, 2005

Related U.S. Application Data

(60) Provisional application No. 60/581,675, filed on Jun. 22, 2004.

(51) Int. Cl.
*A61B 8/00* (2006.01)
(52) U.S. Cl. .................. 600/437; 600/440; 382/128; 73/596; 367/153
(58) Field of Classification Search .................. 600/437, 600/400; 382/128, 276, 277, 285, 305; 345/539, 345/545, 546; 73/596; 367/153–157
See application file for complete search history.

(56) References Cited

U.S. PATENT DOCUMENTS

| 5,315,999 A | 5/1994 | Kinicki et al. |
|---|---|---|
| 5,398,691 A | 3/1995 | Martin et al. |
| 5,546,807 A | 8/1996 | Oxaal et al. |
| 5,562,097 A | 10/1996 | Yao |
| 5,934,288 A * | 8/1999 | Avila et al. .................. 600/443 |
| 5,964,707 A | 10/1999 | Fenster et al. |
| 6,048,312 A * | 4/2000 | Ishrak et al. ................. 600/443 |

(Continued)

FOREIGN PATENT DOCUMENTS

WO   WO 00/58754 A   10/2000

(Continued)

OTHER PUBLICATIONS

European Search Report, dated Oct. 12, 2005, Application No. 05253581.2-2305 PCT, Reference No. 158785/10751, issued by the European Patent Office, 3 pgs.

*Primary Examiner*—Brian Casler
*Assistant Examiner*—Parikha S Mehta
(74) *Attorney, Agent, or Firm*—The Small Patent Law Group; Dean D. Small

(57) ABSTRACT

An ultrasound system is provided that includes a display processor that accesses data volumes stored in an image buffer successively to control generation of at least one of 2D and 3D renderings based on display parameters. The display processor obtains from the image buffer a first data volume defined based on first scan parameter values, while a probe acquires ultrasound information for a second data volume that is entered into the image buffer. The second data volume is defined based on second scan parameter values. A navigation view presents in real time the renderings generated by the display processor with their corresponding 3D orientation. A navigator is provided that controls the display of the navigation view in real time such that, as the user adjusts a display parameter value to change a view plane, images presented in the navigation view are updated to reflect the view plane.

22 Claims, 5 Drawing Sheets

U.S. PATENT DOCUMENTS

| | | |
|---|---|---|
| 6,186,948 B1 | 2/2001 | Kamiyama et al. |
| 6,241,675 B1 * | 6/2001 | Smith et al. .................. 600/443 |
| 6,245,017 B1 * | 6/2001 | Hashimoto et al. .......... 600/447 |
| 6,276,211 B1 | 8/2001 | Smith |
| 6,413,219 B1 * | 7/2002 | Avila et al. .................. 600/443 |
| 6,488,629 B1 | 12/2002 | Saetre et al. |
| 6,554,770 B1 | 4/2003 | Sumanaweera et al. |
| 6,602,194 B2 * | 8/2003 | Roundhill et al. ........... 600/443 |
| 6,641,536 B2 | 11/2003 | Hossack et al. |
| 6,669,641 B2 | 12/2003 | Poland et al. |
| 6,673,018 B2 | 1/2004 | Friedman |
| 6,733,448 B2 | 5/2004 | Kelly et al. |
| 6,755,788 B2 * | 6/2004 | Demers et al. ............... 600/447 |
| 2003/0220569 A1 | 11/2003 | Dione et al. |
| 2004/0019270 A1 | 1/2004 | Takeuchi |

FOREIGN PATENT DOCUMENTS

| | | |
|---|---|---|
| WO | WO 2004/029655 A | 4/2004 |

* cited by examiner

METHOD AND SYSTEM FOR PERFORMING REAL TIME NAVIGATION OF ULTRASOUND VOLUMETRIC DATA

CROSS REFERENCE TO RELATED APPLICATIONS

This application claims priority to and the benefit of the filing date of U.S. Provisional Application No. 60/581,675 filed on Jun. 22, 2004 and which is hereby incorporated by reference in its entirety.

BACKGROUND OF THE INVENTION

The present invention relates to diagnostic ultrasound methods and systems. In particular, the present invention relates to methods and systems for navigation in ultrasound data.

Numerous ultrasound methods and systems exist for use in medical diagnostics. Various features have been proposed to facilitate patient examination and diagnosis based on ultrasound images of the patient. For example, certain systems offer ultrasound volumetric imaging of an object, e.g. the human heart. To be useful, these systems require a navigator for orienting view planes within the volume data. Typically, the navigation of the view planes must be done after data acquisition.

Heretofore, ultrasound methods and systems were unable to acquire volumetric ultrasound data at the same time as an operator navigates in the volumetric data to generate 2D or 3D rendered images of the object.

A need exists for improved methods and systems that provide real time navigation in ultrasound volumetric data.

BRIEF DESCRIPTION OF THE INVENTION

One embodiment, an ultrasound system is provided that includes a probe having a 2D array of transducers for acquiring ultrasound information along a plurality of scan lines through an object in real time. The scan lines are arranged to define volumetric data corresponding to a volume of interest (VOI) in a subject or patient. One such VOI may include the human heart or some portion of the human heart. The system includes a beamformer configured with scan parameter values that define the scan lines. An image buffer stores multiple data volumes acquired over time that are successively retrieved and processed by a display processor. The display processor accesses the data volumes stored in the image buffer successively to control generation of at least one of 2D and 3D renderings based on display parameters, wherein the display processor obtains from the image buffer a first data volume defined based on first scan parameter values, while the probe acquires ultrasound information for a second data volume that is entered into the image buffer. The second data volume is defined based on second scan parameter values. A navigation view presents in real time the renderings generated by the display processor with their corresponding 3D orientation. A navigator is provided that controls the display of the navigation view in real time such that, as the user adjusts a display parameter value to change a view plane, images presented in the navigation view are updated to reflect the view plane. A user interface is provided for adjusting the scan and display parameter values.

In another embodiment, an ultrasound method is provided that acquires ultrasound information, utilizing a 2D array of transducers, along a plurality of scan lines through an object in real time, the scan lines being arranged to define data volumes within the object. The method includes defining the scan lines based on scan parameter values. The method stores multiple data volumes successively acquired over time in an image buffer, and includes adjustment of the values for the scan parameters. At least one of 2D and 3D images is presented based on the data volumes. The method accesses the data volumes stored in the image buffer successively to control presentation of the at least one of 2D and 3D images based on display parameters, wherein a first data volume defined based on first scan parameter values is obtained from the image buffer, while acquiring ultrasound information for a second data volume that is entered into the image buffer, the second data volume being defined based on second scan parameter values.

In yet another embodiment, an ultrasound system is provided that includes a probe having a 2D array of transducers for acquiring ultrasound information along a plurality of scan lines through an object in real time, the scan lines being arranged to define data volumes within the object. A beamformer having scan parameters that define the scan lines is provided, the scan parameters having parameter values. An image buffer stores multiple data volumes successively acquired over time. A display is provided for presenting at least one of 2D and 3D images based on the data volumes. A display processor accesses the data volumes stored in the image buffer successively to control presentation of the at least one of 2D and 3D images based on display parameters. A navigator is also provided that controls display of a navigation view in real time such that, as the user adjusts a display parameter value to change an orientation view, images presented on the display are updated to reflect the orientation view.

DETAILED DESCRIPTION OF THE INVENTION

Figure 1:
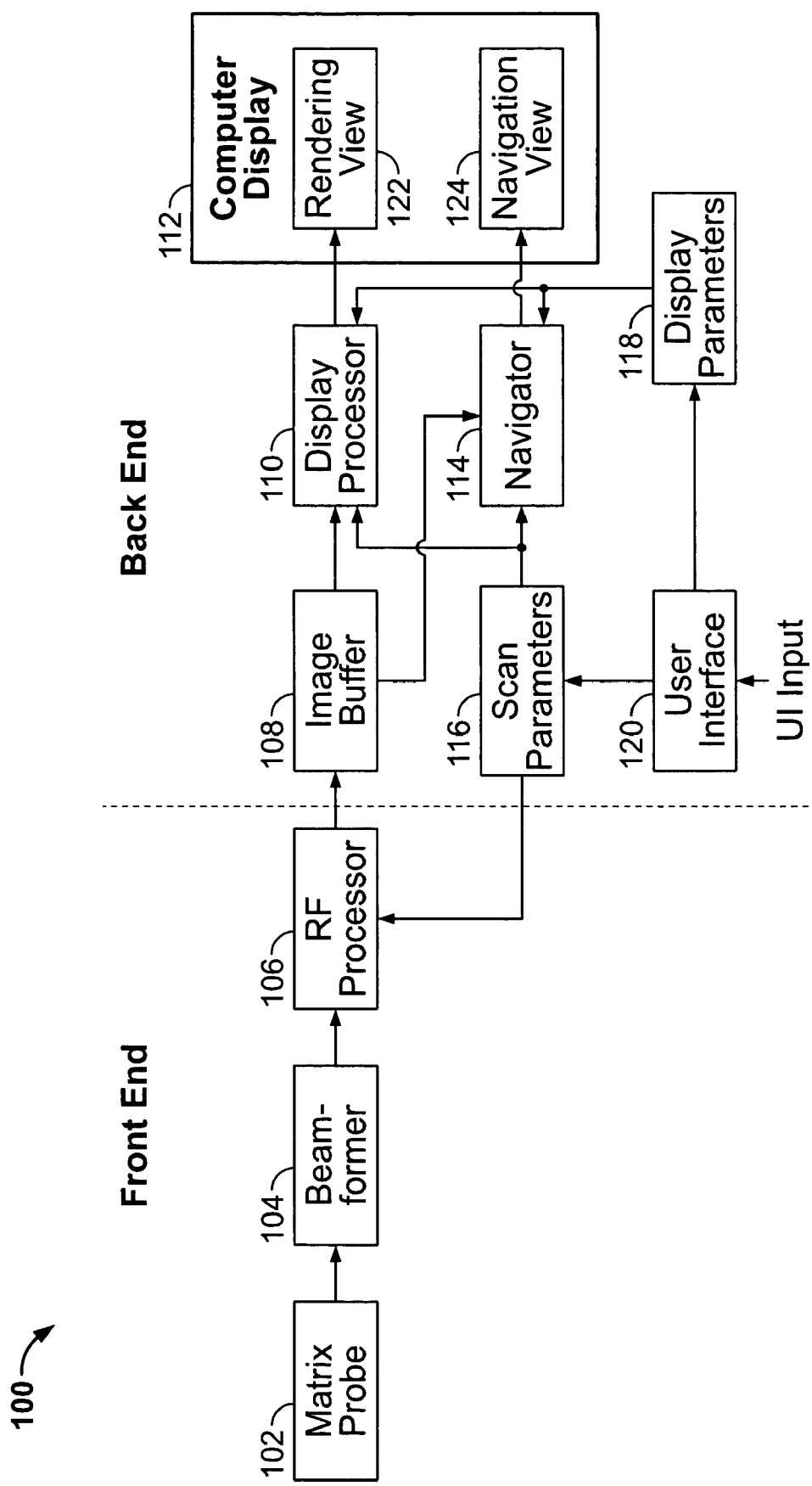
FIG. 1 is a block diagram of an ultrasound system formed in accordance with an embodiment of the present invention.

FIG. 1 is a block diagram of an ultrasound system 100 formed in accordance with an embodiment of the present invention. The ultrasound system 100 is configurable to acquire volumetric data corresponding to a volume of interest (VOI) in a subject or patient. One such VOI may include the human heart or some portion of the human heart. The ultrasound system 100 is configurable to acquire 3-dimensional (3D) volumes of data, each volume defined by an azimuth angle and elevation angle. The ultrasound system 100 includes a 2-dimensional (2D) array/matrix probe 102 that under the guidance of a beamformer 104 scans the VOI and acquires volumes of data at a rate of 15-30 volumes/sec, depending on the size of the volume (azimuth angle and elevation angle). The probe 102 receives backscattered echoes from the scanned object within the VOI and generates electrical receive signals that are combined in the beamformer 104 to form each beam/line within each scan plan. Multiple scan plans (differentiated by their elevation angle) combine to form a volume. The beamformer 104 outputs the beam information to an RF processor 106 that converts the beam information into ultrasoundimaging data, e.g. B-mode information. The B-mode information generated from the RF processor 106 is stored in an image buffer 108. The image buffer 108 is a ring buffer that stores each acquired volume at a rate depending upon the size of each volume. Each volume in the image buffer 108 is given a time stamp.

While B-mode information is stored in the image buffer 108, previously stored B-mode information is retrieved and made available, a volume at a time, to a display processor 110 and a navigator 114. The display processor 110 and the navigator 114 receive the same set of inputs, e.g. a set of scan parameters 116, a set of display parameters 118, and volume data from the image buffer 108 for processing. The image buffer 108 is a ring buffer in that the buffer 108 wraps around on itself. When the last storage location in the buffer 108 is reached, the beginning location in the buffer 108 is next addressed. Volumetric information is retrieved from the buffer 108 by the display processor 110 and the navigator 114 at a rate that prevents overwriting of information in the image buffer 108.

The display processor 110 processes the volume information retrieved from the image buffer 108 to form a rendering such as, for example, a volume rendering or a slice (cut) plane rendering, that is displayed in a rendering view 122 of a computer display 112. The rendering view 122 displays an image of the scanned object as would be seen from a desired orientation or view plane (direction of view) as determined by the display parameters 118. The orientation or view plane from which the rendering view 122 is formed and displayed may be displayed to the user by a navigation view 124 in the computer display 112. The navigator 114 generates and controls the navigation view 124 that is displayed on the computer display 112. The navigation view 124 may show a high level view of the scanned object and the orientation or direction of view of the scanned object by positioning the scanned object with respect to a set of planes or slices, such as a set of orthogonal planes or slices that form a Cartesian reference system.

The user through a user interface 120 may change the scan parameters 116 and/or the display parameters 118. The navigator 114 controls the orientation shown in the navigation view 124 based on the values of the display parameters 118. When changing the navigation view 124 by changing the display parameters 118, the display of the rendering view 122 is correspondingly changed to show the scanned object as formed and seen from the new view direction and/or orientation. Thus, the user may navigate and change the direction of view and/or orientation of the scanned object as is displayed in the navigation view 124, and in so doing, change the view of the scanned object that is displayed in the rendering view 122. The display of the scanned object shown in rendering view 122 is aligned to agree and correspond with the new view orientation that is shown in the navigation view 124. Direction of view (the navigation view 124) may be changed while new volume data is being acquired and stored in the image buffer 108. The user is able to navigate in real time the view or perspective being displayed of the scanned object while the object is being scanned. The lag time to see changes made in the display parameters 118 (changes in the viewing direction and/or orientation) update the rendering view 122 and the navigation view 124 depends on the time required to generate new renderings. Unlike changing the scan parameters 116, changing the display parameters 118 does not affect the configuration of the beamformer 104.

Figure 2:
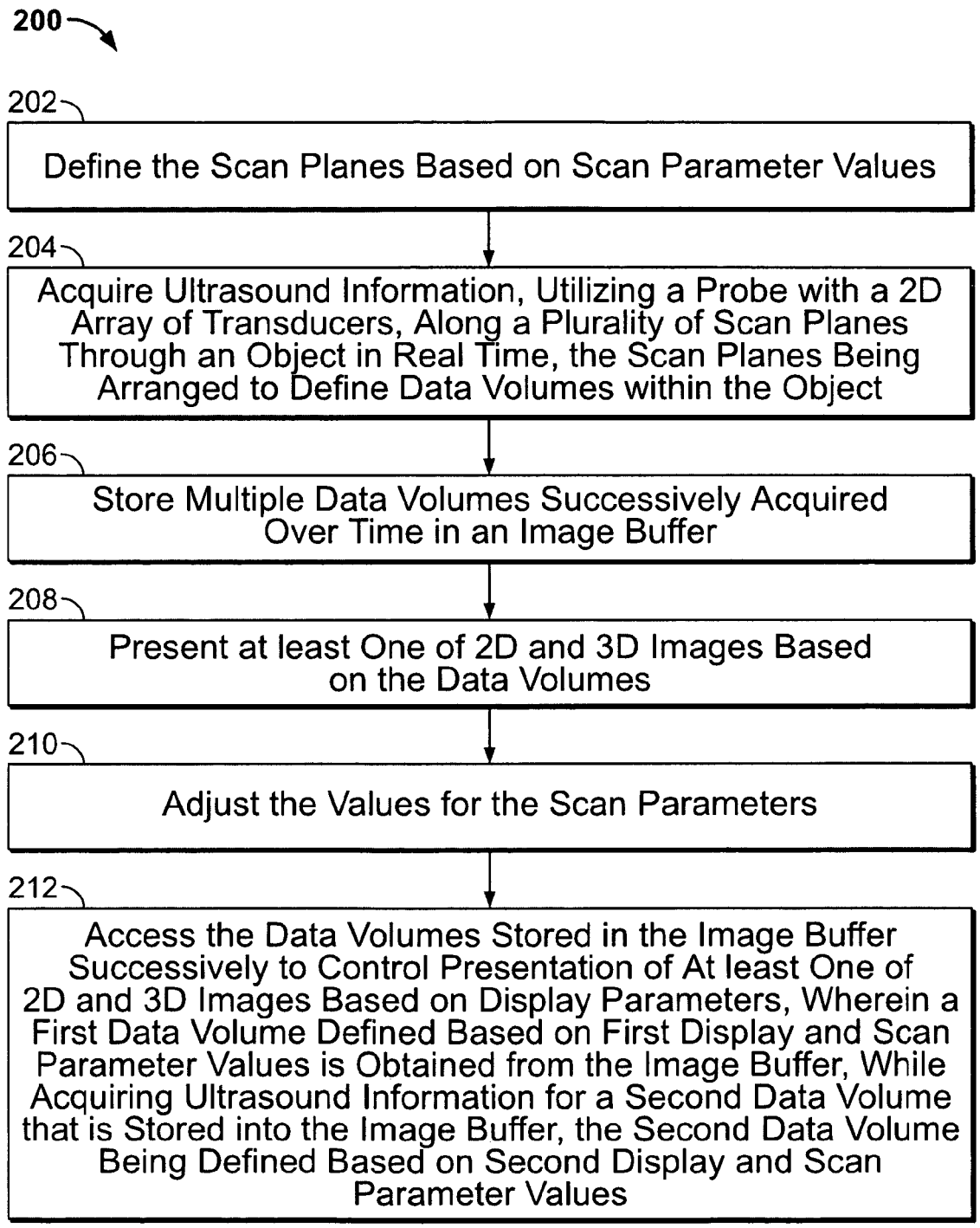
FIG. 2 is a flowchart of an exemplary method supporting real time navigation of 2D and 3D rendering views produced and displayed from acquired volumetric data.

FIG. 2 is a flowchart 200 of an exemplary method supporting real time navigation of 2D and 3D rendering views 122 produced and displayed in the computer display 112 from acquired volumetric data. At 202, a plurality of scan planes is defined based on values assigned to the scan parameters 116. The scan parameters 116 include such variables as, for example, scan depth, width (azimuth angle), elevation angle, number of beams (beam density) in elevation and in azimuth, number of samples/beam, and mode. The user may define the values for the scan parameters 116 through the user interface 120, such as through the use of a keyboard, trackball, and/or mouse, and may update the scan parameters 116 in real time during the ultrasound scanning. New scan parameter values are provided to the display processor 110 and the navigator 114. The lag time for seeing the effect of having changed the values of the scan parameters 116 is from 1 to 2 seconds, time being needed to configure the beamformer 104 with the new scan parameters 116.

At 204, ultrasound information is acquired by utilizing a probe with a 2D array of transducers to collect scan information along a plurality of scan plans through a scanned object. The scanning is performed in real time in that no manual repositioning of the probe is needed in order to acquire all the scan planes that form a data volume. Each scan plan of the volume is differentiated from another by the elevation angle of the beam lines producing the scan plan. The width of the scan plan is determined by an azimuth angle. A volume of scan data may be produced by varying the elevation angle of the scan to generate a plurality of scan planes through the scanned object at different elevations.

At 206, multiple data volumes are successively stored as acquired over time in the image buffer 108. As related for FIG. 1, the image buffer 108 is a ring buffer with data volumes being extracted and used by the display processor 110 and the navigator 114 while data volumes are being stored in the image buffer 108.

At 208, the 2D or 3D rendering view 122 is presented in the computer display 112 as formed by the display processor 110 based on the scanned volume, the scan parameters 116, and the display parameters 118. At 210 the user may adjust the scan parameters 116 to obtain a wider or narrower scan of the scanned object, or to obtain a scan with a greater density of beams/lines in a scan plane or the elevation (number of scan planes/per volume).

At 210, the user adjusts the scan parameters 116 and, as the user makes adjustments, the effects of the adjustments as displayed in the rendering view 122 are presented 208 in the computer display 112. The effects of the adjustments to the scan parameters 116 may be viewed in about 1 or 2 seconds from having entered the adjustments. The time of 1 or 2 seconds may be needed in order to reconfigure the beamformer 104 with the new scan parameters 116, acquire and store new volume data in the image buffer 108, retrieve and process the new volume data from the image buffer 108 by the display processor 110, and present the updated rendering view 122 in the computer display 112. When the user is satisfied with the size and quality of display of the scanned object in the rendering view 122, the user may want to view the scanned object from a different direction and/or orientation.

At 212, data volumes are successively accessed from the image buffer 108, and with the current valuing of the scan parameters 116 and the display parameters 118, the rendering view 122 and the navigation view 124 are displayed in the computer display 112. The navigator 114 uses the display parameters 118 to define the orientation or direction of view (view plane) and to display the view plane as part of the navigation view 124 in the computer display 112. The user may adjust the display parameters 118 through the user interface 120 similarly to how the scan parameters 116 are adjusted. Examples of display parameters may include view direction, rotation translation, tilt, zoom factor, and number of images viewed. Both the display processor 110 and the navigator 114 read the display parameters 118. The navigator 114 produces a view plane or angle of view with a view of the scanned object in the navigation view 124. The rendering view 122 may be an enlarged view of the scanned object in comparison to the scanned object shown in the navigation view 124. The rendering view 122 and the navigation view 124 may each be displayed in a quadrant of the computer display 112.

Real time navigation is obtained by successively accessing data volumes stored in the image buffer 108 and scan parameter values stored in 116 and presenting at least one of 2D and 3D images based on display parameters 118, wherein each image that is displayed is defined based on separate display parameter values stored in display parameters 118.

Figure 3:
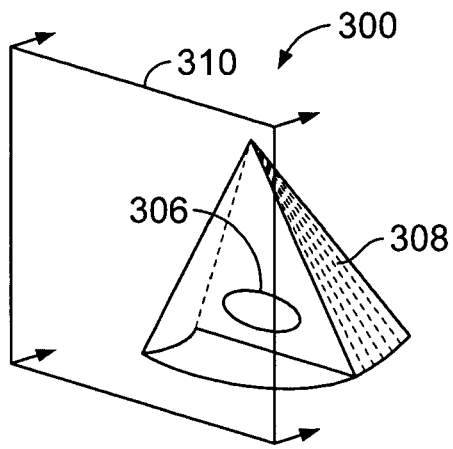
FIG. 3 is an illustration of a navigation view with a view plane looking into a volume from the left that may be produced by the system of FIG. 1.

FIG. 3 is an illustration of a navigation view 300 with a view plane 310 looking into a volume 308 from the left that may be produced by the system 100 of FIG. 1. The navigation view 300 shows an image of a heart valve 306 generated as seen from viewing into a volume 308 from the left. The view plane 310, is shown as a table top with four arrows for legs, and indicates to the user that the image of the heart valve 306 is produced by looking perpendicularly through the view plane 310 (perpendicularly through the table top) into the volume 308. The image of the heart valve 306 may be formed by use of various techniques, such as slice (cut plane) imaging, surface rendering, and the like. The user may change the orientation of the view plane 310 with respect to the volume 308 by rotating and/or translating the view plane 310. For example, the view plane 310 may be reoriented about the volume 308 to obtain a view plane 312 and view of the heart valve 306 as shown in FIG. 4.

Figure 4:
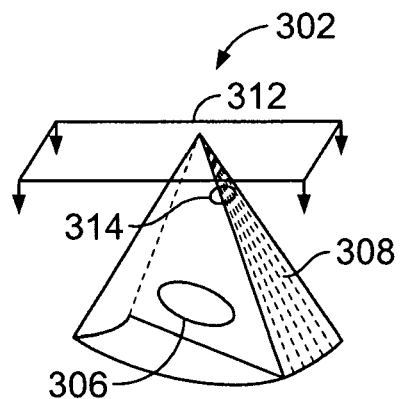
FIG. 4 is an illustration of a navigation view with a view plane looking into the volume of FIG. 3 from the top.

FIG. 4 is an illustration of a navigation view 302 with a view plane 312 looking into the volume 308 from the top. A translation and/or rotation of the view plane 310 of FIG. 3 obtains the view plane 312 of FIG. 4. Shown in FIG. 4 is an object 314 between the view plane 312 and the heart valve 306. The view from the view plane 312 includes the object 314 which may obstruct the view of a portion of the heart valve 306. The generated image of the heart valve 306 has the object 314 obstructing the view of the heart valve 306. The obstructed view may be resolved by translating the view plane 312 downward as shown in FIG. 5.

Figure 5:
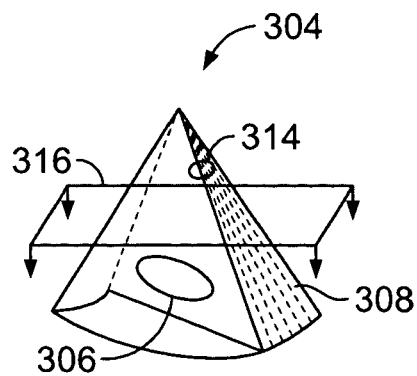
FIG. 5 is an illustration of the navigation view of FIG. 4 with the view plane translated downwards.

FIG. 5 is an illustration of the navigation view 302 of FIG. 4 with the view plane 312 translated downward. The view plane 312 of navigation view 302 has been lowered down (translated downward) to be closer to the heart valve 306 in FIG. 5. The new view plane 316 is positioned below the obstructing object 314 to result in an image of the heart valve 306 that is no longer obstructed by the object 314. By translating the view plane 312 downward to obtain the view plane 316, the user has eliminated use of the volumetric scan data that contains the obstructing object 314 in forming the view or image of the heart valve 306. The user may change the values of display parameters 118 through the use of the user interface 120 of FIG. 1 to reorient the view plane 312. Reorientation may result in a view of the heart valve 306 from a different angle and/or without obstructing objects within the view.

Figure 6:
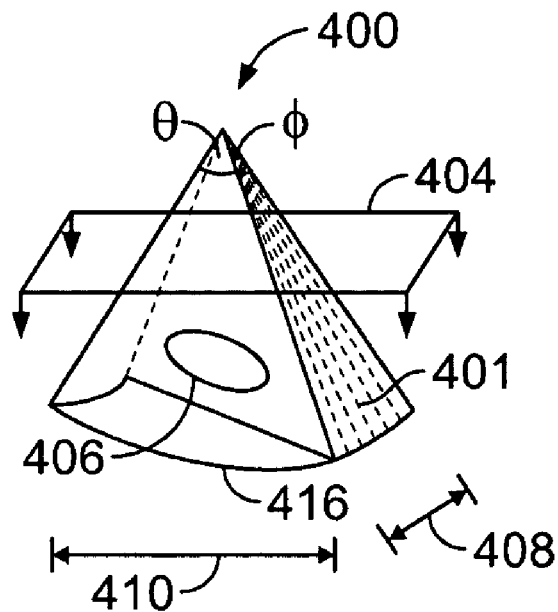
FIG. 6 is an illustration showing a volume obtained with a selected width and elevation, the width and elevation selected through a user interface of the system of FIG. 1.

FIG. 6 is an illustration 400 showing a volume 401 obtained with a selected width 410 (azimuth angle $\theta$) and elevation 408 (elevation angle $\phi$), the width 410 and elevation 408 selected by the user through the user interface 120 of the system 100 of FIG. 1. The volume 401 is determined from the width 410 (the azimuth angle $\theta$) of a scan slice 416 and the elevation 408 (the elevation angle $\phi$) for the scan slice 416. FIG. 6 shows a view plane 404 through which an image of a heart valve 406 is defined and displayed. When observing the display of the heart valve 406, the user or sonographer may desire to display more of the heart valve 406 or more area surrounding the heart valve 406, but with the view remaining unchanged. A larger view of the heart valve 406 may be obtained as shown in FIG. 7.

Figure 7:
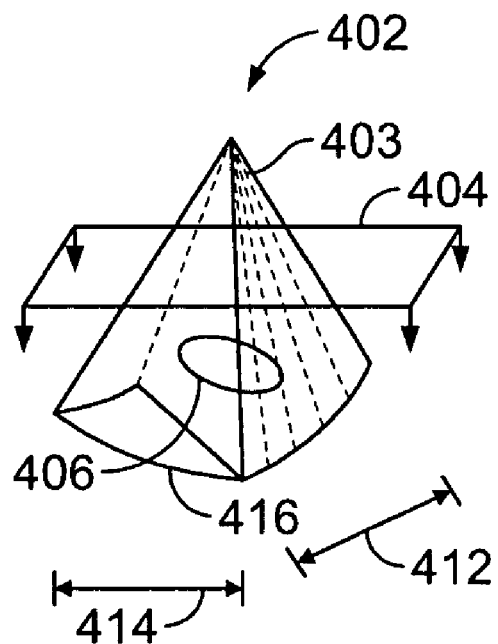
FIG. 7 is an illustration showing a changed volume obtained by changing the width and elevation for the volume of FIG. 6.

FIG. 7 is an illustration 402 showing a changed volume 403 obtained by changing the width 410 and elevation 408 for the volume 401 of FIG. 6. In FIG. 7, a shortened width 414 and increased elevation 412 through which scan slices 416 are obtained is specified by the user to obtain the changed volume 403. Without changing the view plane 404 of FIG. 6, a larger view of the heart valve 406 is obtained by increasing the volume 403 of the scan.

Figure 8:
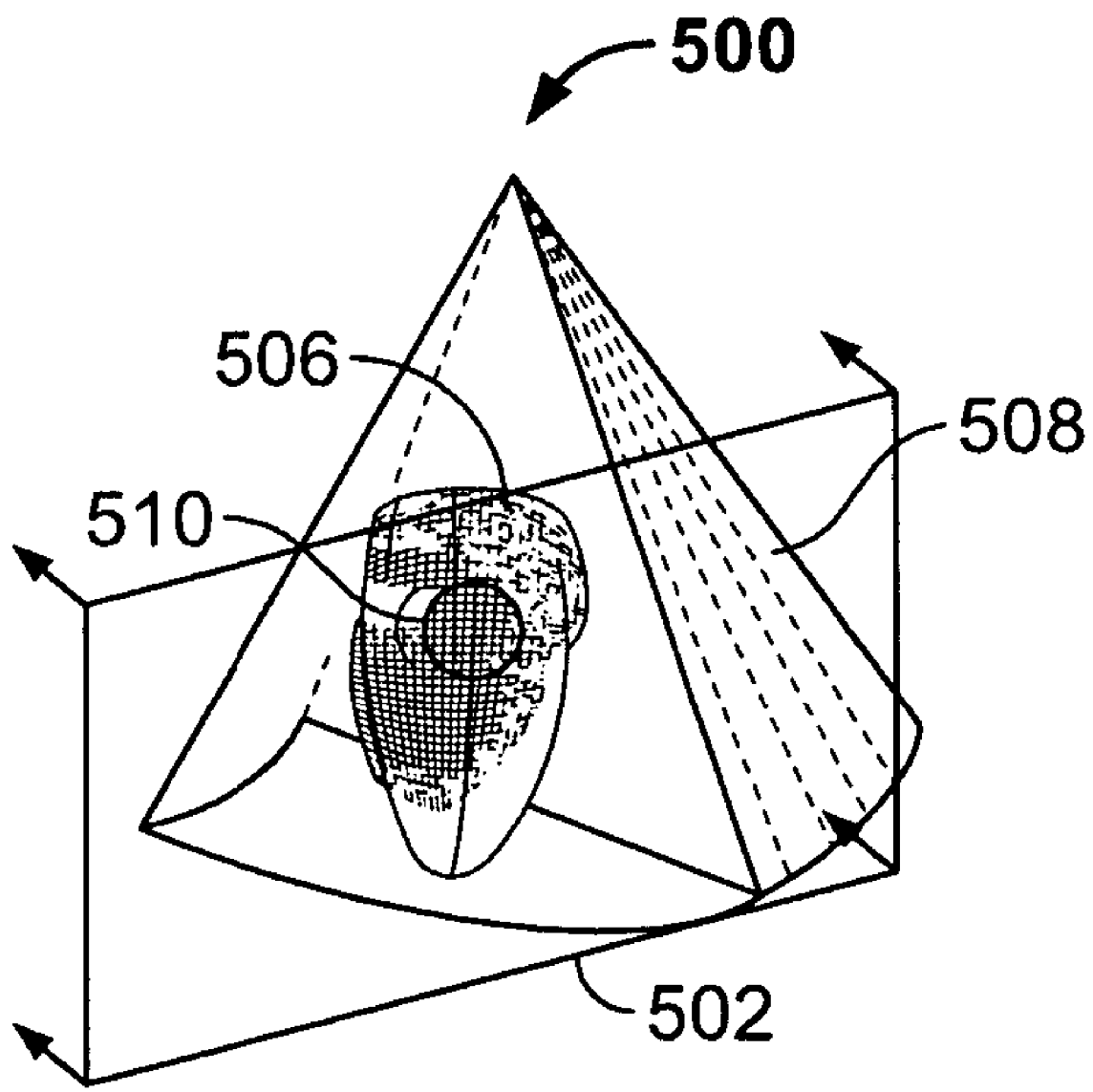
FIG. 8 is an illustration of a navigation view of a heart as seen from a view plane selected by the user of the system of FIG. 1.

FIG. 8 is an illustration of a navigation view 500 of a heart 506 as seen from a view plane 502 selected by the user of the system 100 of FIG. 1. The heart 506 is shown with an aortic structure 510 facing the view plane 502. The image of the heart 506 in the navigation view 500 may be generated as a surface rendering. In an alternative embodiment, the image shown of the heart 506 may not be a generic surface model, but instead may be a calibrated model of a heart.

The system 100 may generate a model of a heart constructed from a plurality of polygons and position the heart model in the location of the heart 506. To be useful, the heart model is scaled based on data from the patient. Data may be manually measured or automatically determined to scale the size of the heart model based on actual size of the patient's heart. For example, the actual size of the patient's heart may be determined based on three landmarks in data (e.g. two points on the mitral ring and the aortic output) and apex. The generated heart model is positioned and oriented within the volume 508 according to the landmarks in the volume data. Thus, the navigation view 500 may show a heart 506 that is a calibrated scale model of the patient's heart positioned and oriented correctly within the volume 508. Corresponding to the view plane 502 of the navigation view 500, a rendering view (not shown in the figure) may show 2D or 3D images derived from the ultrasound scan data. The view plane 502 may intersect the heart model.

Exemplary embodiments of diagnostic ultrasound systems and methods are described above in detail. The systems and methods are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. An ultrasound system, comprising:
a probe having a 2D array of transducers acquiring ultrasound information along a plurality of scan lines through an object in real time, said scan lines being arranged to define data volumes within the object;
a beamformer having scan parameters that define said scan lines, said scan parameters having parameter values;
an image buffer storing multiple data volumes successively acquired over time;
a display processor accessing said data volumes stored in said image buffer successively to control generation of at least one of 2D and 3D renderings based on display parameters. wherein said display processor obtains from said image buffer a first data volume defined based on first scan parameter values, while said probe acquires ultrasound information for a second data volume that is entered into said image buffer, said second data volume being defined based on second scan parameter values;
a navigation view presenting in real time the said renderings generated by said display processor with their corresponding 3D orientation;
a navigator controlling display of said navigation view in real time such that, as the user adjusts a display parameter value to change a view plane, images presented in said navigation view are updated to reflect said view plane; and
a user interface configure to adjust said scan and display parameter values.

2. The ultrasound system of claim 1, wherein said user interface permits a user to adjust said scan parameters from said first parameter values to said second parameter values while viewing said at least one of 2D and 3D renderings based on volume data being acquired in real time.

3. The ultrasound system of claim 1, wherein said image buffer simultaneously stores at least one data volume defined by said first parameter values and at least one data volume defined by said second parameter values.

4. The ultrasound system of claim 1, wherein said image buffer is substantially simultaneously accessed by said display processor to read said data volumes from said image buffer and by said beamformer to write said data volumes to said image buffer.

5. The ultrasound system of claim 1, wherein said display presents at least one of volume rendered images, surface rendered images and cut plane images.

6. The ultrasound system of claim 1, further comprising a navigator controlling display of a navigation view indicating at least one of view planes, object models and landmarks relative to the said data volume, said navigation view being defined based on said data volume data, scan and display parameter values.

7. The ultrasound system of claim 1, wherein said probe continues to acquire new data volumes as display parameters values for said display parameters are changed.

8. The ultrasound system of claim 1, wherein a lag time after changing display parameter values before displaying updated images based on new display parameter values is no more than ¼ second.

9. The ultrasound system of claim 1, wherein a lag time after changing scan parameter values before displaying updated images based on new scan parameter values is no more than 2 seconds.

10. The ultrasound system of claim 1, wherein said image buffer stores a time stamp with each of said data volumes, said time stamp identifying a time at which said data volume was acquired.

11. The ultrasound system of claim 1, wherein said navigation view presenting in real time the said renderings generated by said display processor with their corresponding 3D orientation comprises a visual indicator of a view plane superimposed on a 3D rendering, the visual indicator showing a view perpendicularly through the view plane as displayed in a rendering view and arrows indicating the direction of the view.

12. The ultrasound system of claim 1, wherein said data volumes stored in said image buffer comprise images of a heart and further comprising a navigation view controlled by the navigator and displaying a surface rendering of the heart that is a calibrated scale model of the heart of a patient that is positioned and oriented correctly within the displayed volume, 13. An ultrasound method, comprising:
acquiring ultrasound information, utilizing a 2D array of transducers, along a plurality of scan lines through an object in real time, said scan lines being arranged to define data volumes within the object;
defining said scan lines based on scan parameters having scan parameter values;
storing multiple data volumes successively acquired over time in an image buffer;
adjusting said scan parameter values for said scan parameters;
presenting at least one of 2D and 3D images based on said data volumes; and
accessing said data volumes stored in said image buffer successively to control presentation of said at least one of 2D and 3D images based on display parameters, wherein a first data volume defined based on first scan parameter values is obtained from said image buffer, while acquiring ultrasound information for a second data volume that is entered into said image buffer, said second data volume being defined based on second scan parameter values.

14. The ultrasound method of claim 13, further comprising permitting a user to adjust said scan parameters from said first parameter values to said second parameter values while viewing 2D images being acquired in real time.

15. The ultrasound method of claim 13, further comprising simultaneously storing at least one data volume defined by said first parameter values and at least one data volume defined by said second parameter values.

16. The ultrasound method of claim 13, further comprising substantially simultaneously accessing said image buffer to read said data volumes from said image buffer and writing said data volumes to said image buffer.

17. The ultrasound method of claim 13, further comprising presenting at least one of volume rendered images, surface rendered images and cut plane images.

18. The ultrasound method of claim 13, further comprising controlling display of a navigation view indicating at least one of view planes, object models and landmarks relative to said data volume, said navigation view being defined based on said data volume, scan and display parameter values.

19. The ultrasound method of claim 13, further comprising continuing to acquire new data volumes as display parameters values for said display parameters are changed.

20. The ultrasound method of claim 13, wherein a lag time after changing display parameter values before displaying updated images based on new display parameter values is no more than ¼ second.

21. The ultrasound method of claim 13, wherein a lag time after changing scan parameter values before displaying updated images based on new scan parameter values is no more than 2 seconds.

22. The ultrasound method of claim 13, further comprising storing a time stamp with each of said data volumes, said time stamp identifying a time at which said data volume was acquired.

* * * * *

UNITED STATES PATENT AND TRADEMARK OFFICE
CERTIFICATE OF CORRECTION

PATENT NO. : 7,604,595 B2 Page 1 of 1
APPLICATION NO. : 10/926547
DATED : October 20, 2009
INVENTOR(S) : Steen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1455 days.

Signed and Sealed this

Fifth Day of October, 2010

David J. Kappos
*Director of the United States Patent and Trademark Office*